(12) United States Patent
Shono et al.

(10) Patent No.: US 8,830,460 B2
(45) Date of Patent: Sep. 9, 2014

(54) OPTICAL MEASUREMENT APPARATUS AND PROBE

(71) Applicant: Olympus Corporation, Tokyo (JP)

(72) Inventors: Yuki Shono, Hachioji (JP); Hideyuki Takaoka, Hachioji (JP); Ryosuke Ito, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/870,396

(22) Filed: Apr. 25, 2013

(65) Prior Publication Data

US 2013/0235384 A1   Sep. 12, 2013

Related U.S. Application Data

(63) Continuation of application No. PCT/JP2011/074567, filed on Oct. 25, 2011.

(60) Provisional application No. 61/408,176, filed on Oct. 29, 2010.

(51) Int. Cl.
*G01N 21/00* (2006.01)
*A61B 5/00* (2006.01)
*G01N 21/47* (2006.01)
*G01B 9/02* (2006.01)

(52) U.S. Cl.
CPC .......... *G01B 9/02091* (2013.01); *A61B 5/0084* (2013.01); *G01N 21/474* (2013.01); *G01N 2021/4719* (2013.01); *A61B 5/0075* (2013.01)
USPC ........................................................ 356/337

(58) Field of Classification Search
USPC ........................................................ 356/337
See application file for complete search history.

(56) References Cited

U.S. PATENT DOCUMENTS

| | | | |
|---|---|---|---|
| 4,669,467 | A | 6/1987 | Willett et al. |
| 6,144,791 | A | 11/2000 | Wach et al. |

(Continued)

FOREIGN PATENT DOCUMENTS

| | | |
|---|---|---|
| JP | A-9-21963 | 1/1997 |
| JP | A-9-117407 | 5/1997 |

(Continued)

OTHER PUBLICATIONS

Mutyal et al., "Design and Implementation of Fiber Optic Probe for measuring Field Effect of Carcinogenesis with Low-Coherence Enhanced Backscattering Spectroscopy (LEBS)," *Biomedical Optics*, 2010.

(Continued)

*Primary Examiner* — Tu Nguyen
(74) *Attorney, Agent, or Firm* — Oliff PLC

(57) ABSTRACT

An optical measurement apparatus that measures a property of a scatterer, including: a light source that supplies illumination light having at least one spectral component; an illumination fiber that propagates, to a distal end thereof, light supplied from a proximal end thereof by the light source and illuminates light onto the scatterer from the distal end; first and second light detection fibers, each outputting, from a proximal end thereof, returned light from the scatterer, the returned light entering from a distal end thereof, the first and second light detection fibers having distal end positions different from each other in a longitudinal direction; a detection unit that detects light output from the proximal ends of the first and second light detection fibers; and a measurement unit that measures a property of the scatterer based on a result of the detection by the detection unit.

18 Claims, 18 Drawing Sheets

(56) References Cited

U.S. PATENT DOCUMENTS

| | | | |
|---|---|---|---|
| 7,139,076 B1 * | 11/2006 | Marbach | 356/446 |
| 7,142,307 B1 * | 11/2006 | Stark | 356/446 |
| 7,301,629 B2 * | 11/2007 | Bambot et al. | 356/337 |
| 2004/0181148 A1 | 9/2004 | Uchiyama et al. | |
| 2005/0054937 A1 | 3/2005 | Takaoka et al. | |
| 2008/0037024 A1 | 2/2008 | Backman et al. | |

FOREIGN PATENT DOCUMENTS

| | | |
|---|---|---|
| JP | A-9-248281 | 9/1997 |
| JP | A-2000-510604 | 8/2000 |
| JP | A-2002-535645 | 10/2002 |
| JP | A-2004-121749 | 4/2004 |
| JP | A-2004-177257 | 6/2004 |
| JP | A-2005-40175 | 2/2005 |
| JP | A-2008-39602 | 2/2008 |
| JP | A-2009-537014 | 10/2009 |
| JP | A-2010-158358 | 7/2010 |
| WO | WO 00/43750 A2 | 7/2000 |
| WO | WO 2007/133684 A2 | 11/2007 |

OTHER PUBLICATIONS

International Search Report issued in International Patent Application No. PCT/JP2011/074567 dated Dec. 6, 2011 (w/translation).

* cited by examiner

FIG.1
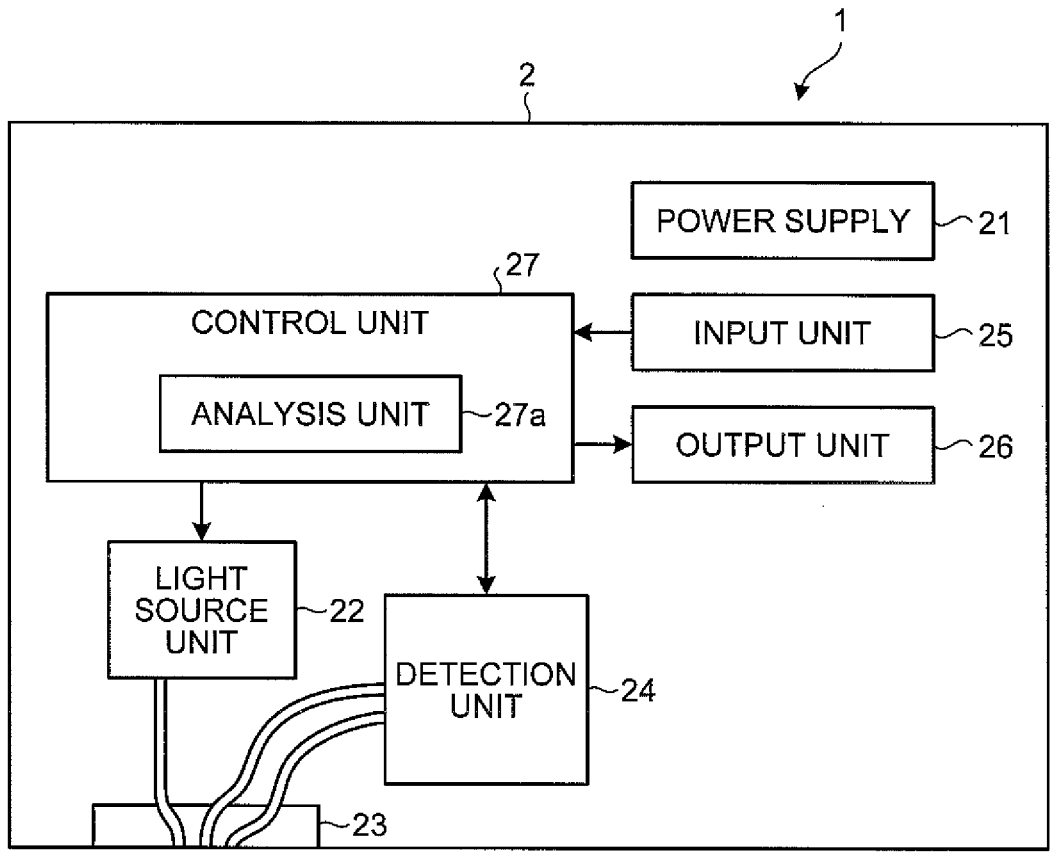
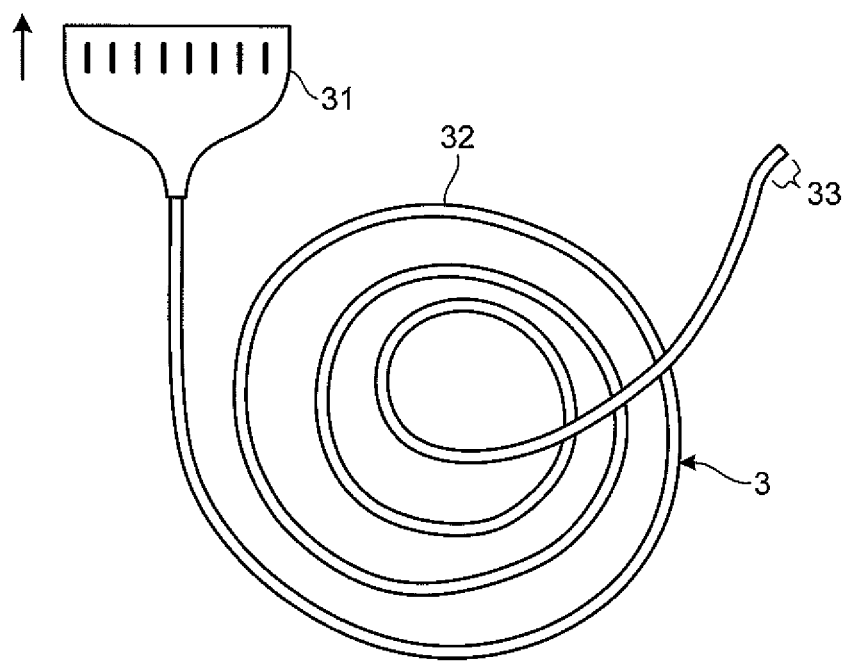

OPTICAL MEASUREMENT APPARATUS AND PROBE

CROSS REFERENCES TO RELATED APPLICATIONS

This application is a continuation of PCT international application Ser. No. PCT/JP2011/074567 filed on Oct. 25, 2011, which designates the United States and claims the benefit of priority from U.S. provisional patent application No. 61/408,176 filed on Oct. 29, 2010, and the entire contents of the PCT international application and the U.S. provisional patent application are incorporated herein by reference.

BACKGROUND OF THE INVENTION

1. Field of the Invention

The present invention relates to an optical measurement apparatus that measures optical properties of a scatterer and a probe for the measurement.

2. Description of the Related Art

In recent years, an optical measurement apparatus has been proposed, which uses a low-coherence enhanced backscattering (LEBS) technique for detecting characteristics of a scatterer by irradiating incoherent light having a short spatial coherence length onto the scatterer from a distal end of a probe and measuring scattered light (for example, see International Patent Publication Pamphlet No. WO 2007/133684). Such an optical measurement apparatus is able to perform optical measurement of a biological tissue, which is a scatterer, in combination with an endoscope for observing internal organs such as digestive organs. When this LEBS technique is used, it is required to detect each of at least two scattered light of different scattering angles.

Conventionally, a configuration for obtaining scattered light having a desired angle with a light detection fiber by providing an optical element such as a lens or a beam splitter at a distal end of a probe (for example, see U.S. Patent Application Publication No. 2008/0037024) or a configuration for obtaining scattered light having a desired angle by separating an illumination fiber from a light detection fiber by a predetermined distance (for example, see Biomedical Optics 2010 BtuD90) has been proposed.

SUMMARY OF THE INVENTION

An optical measurement apparatus according to an aspect of the present invention measures a property of a scatterer, and includes: a light source that supplies illumination light having at least one spectral component; an illumination fiber that propagates, to a distal end thereof, light supplied from a proximal end thereof by the light source and illuminates light onto the scatterer from the distal end; first and second light detection fibers, each of the first and second light detection fibers outputting, from a proximal end thereof, returned light from the scatterer, the returned light entering from a distal end thereof, the first and second light detection fibers having distal end positions different from each other in a longitudinal direction; a detection unit that detects light output from the proximal end of the first light detection fiber and the proximal end of the second light detection fiber; and a measurement unit that measures a property of the scatterer based on a result of the detection by the detection unit.

An optical measurement apparatus according to another aspect of the present invention measures a property of a scatterer, and includes: a light source that supplies illumination light having at least one spectral component; an illumination fiber that propagates light supplied from a proximal end thereof by the light source to a distal end thereof and illuminates light onto the scatterer from the distal end; a light detection fiber that is movable in a longitudinal direction and outputs, from a proximal end thereof, returned light from the scatterer, the returned light entering from a distal end thereof; a detection unit that detects light output from the proximal end of the light detection fiber; a measurement unit that measures a property of the scatterer based on a result of the detection by the detection unit; and a mover that relatively moves the light detection fiber in the longitudinal direction relative to the illumination fiber.

A probe for measurement, according to still another aspect of the present invention, which is detachably connected to an optical measurement apparatus that measures a property of a scatterer, includes: an illumination fiber that propagates, to a distal end thereof, light supplied from a proximal end thereof by a light source and illuminates light onto the scatterer from the distal end; and first and second light detection fibers, each of the first and second light detection fibers outputting, from a proximal end thereof, returned light from the scatterer, the returned light entering from a distal end thereof, the first and second light detection fibers having distal end positions different from each other in a longitudinal direction.

A probe for measurement according to yet another aspect of the present invention, which is detachably connected to an optical measurement apparatus that measures a property of a scatterer, includes: an illumination fiber that propagates light supplied from a proximal end thereof to a distal end thereof and illuminates light onto the scatterer from the distal end; and a light detection fiber that is movable in a longitudinal direction and outputs, from a proximal end thereof, returned light from the scatterer, the returned light entering from a distal end thereof.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 1 is a schematic diagram illustrating a schematic configuration of an optical measurement apparatus according to a first embodiment.

DETAILED DESCRIPTION OF THE PREFERRED EMBODIMENTS

Figure 2:
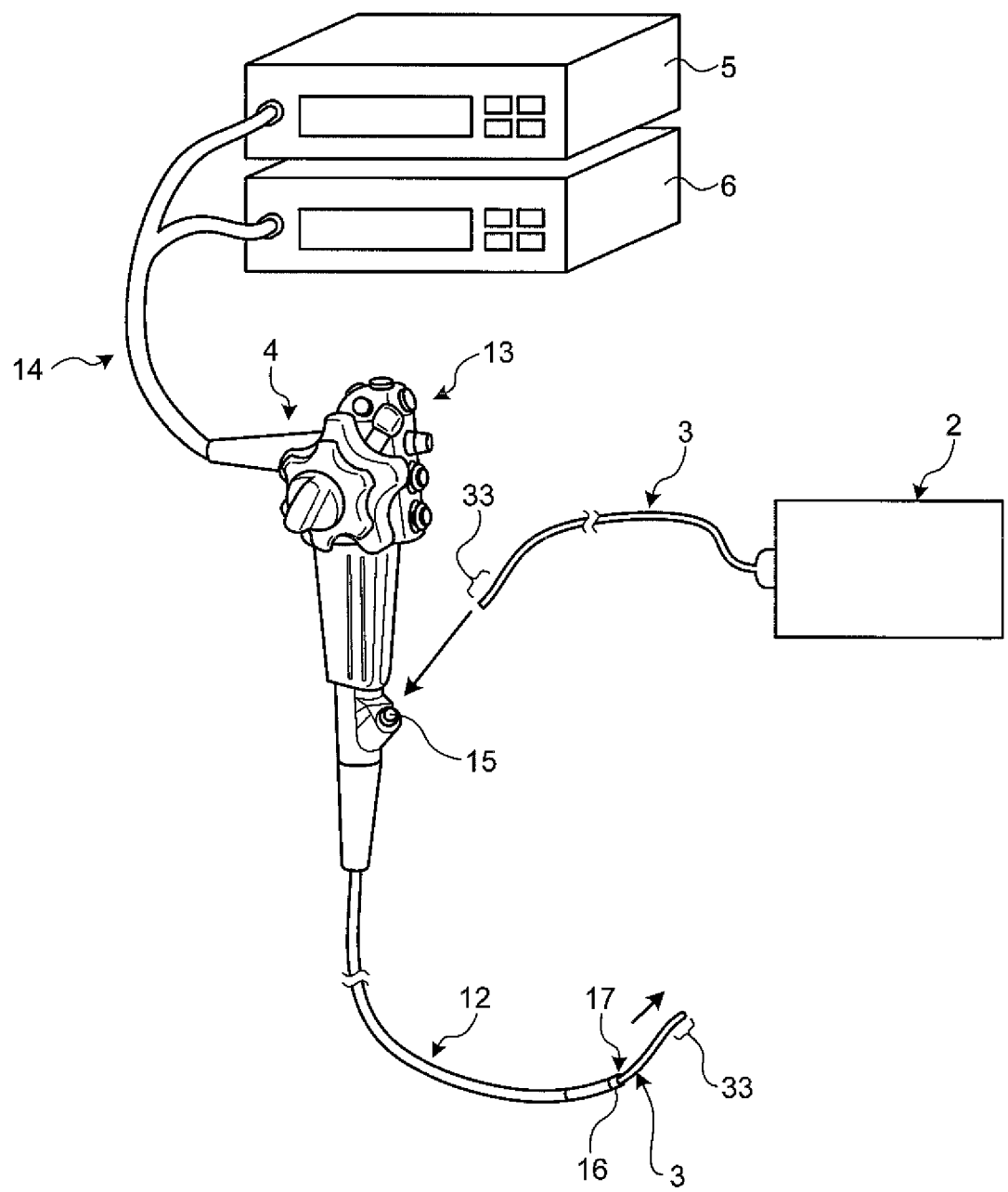
FIG. 2 is a diagram illustrating insertion of a probe illustrated in FIG. 1 into a subject.

Hereinafter, preferred embodiments of an optical measurement apparatus and a probe according to the present invention will be described in detail with reference to the drawings. The invention is not limited by the embodiments. In the description of drawings, like reference numerals denote like elements. Further, it is to be noted that the drawings are schematic, and relations between thicknesses and widths of each element, and ratios among elements are different from those of the actual. Among the drawings also, a same portion having relations or ratios of dimensions different from one another is included.

First Embodiment

FIG. 1 is a schematic diagram illustrating a schematic configuration of an optical measurement apparatus according to a first embodiment of the present invention. As illustrated in FIG. 1, an optical measurement apparatus 1 according to the first embodiment includes a main unit 2 that performs optical measurement on an object to be measured such as a biological tissue, which is a scatterer, and detects characteristics of the object to be measured, and a probe 3 for the measurement, which is inserted into a subject. The probe 3 emits light supplied from a proximal end thereof to the object to be measured from a distal end thereof and outputs scattered light from the object to be measured, the scattered light entering from the distal end, to the main unit 2 from the proximal end.

The main unit 2 includes a power supply 21, a light source unit 22, a connector 23, a detection unit 24, an input unit 25, an output unit 26, and a control unit 27.

The power supply 21 supplies power to each element of the main unit 2.

The light source unit 22 generates light to be illuminated onto the object to be measured. The light source unit 22 includes an incoherent light source such as a white light-emitting diode (LED) or a xenon lamp, and one or more lenses. The light source unit 22 supplies to the probe 3, via the connector 23, incoherent light that has at least one spectral component and that is be illuminated onto the object to be measured.

The connector 23 detachably connects the proximal end of the probe 3 to the main unit 2. The connector 23 supplies, to the probe 3, the light emitted from the light source unit 22, and outputs the scattered light output from the probe 3 to the detection unit 24. The connector 23 outputs, to the control unit 27, information related to whether or not the probe 3 is connected.

The detection unit 24 detects detected light, which is the light output from the probe and is the scattered light from the object to be measured. The detection unit 24 is implemented using an optical detector, a spectrometer, a spectrometer, and the like. The detection unit 24 detects, via the connector 23, the scattered light output from the probe 3, and measures a spectral component, an intensity, and the like of the detected scattered light. The detection unit 24 outputs a result of the measurement to the control unit 27.

The input unit 25 is implemented using a push-type switch or the like, receives instruction information for instructing activation of the main unit 2 and various other types of instruction information, and inputs them into the control unit 27 by manipulation of a switch or the like.

The output unit 26 outputs information related to various processes in the optical measurement apparatus 1. The output unit 26 is implemented using a display, a speaker, a motor, or the like and outputs information related to various processes in the optical measurement apparatus 1 by outputting image information, audio information, or vibration.

The control unit 27 controls processing operations of each element of the main unit 2. The control unit 27 includes a central processing unit (CPU) and a semiconductor memory such as a random access memory (RAM). The control unit 27 controls operations of the main unit 2 by transferring and the like, to respective elements of the main unit 2, instruction information or data. The control unit 27 includes an analysis unit 27a that analyzes characteristics of the object to be measured based on a result of detection by the detection unit 24. That is, the analysis unit 27a functions as a measurement unit.

The probe 3 is implemented using a multiple number of optical fibers. The probe 3 includes a proximal end portion 31 detachably connected to the connector 23 of the main unit 2, a flexible portion 32 having flexibility, and a distal end portion 33 from which the light supplied from the light source unit 22 is emitted and into which the scattered light from the object to be measured enters.

The optical measurement apparatus 1 performs optical measurement in combination with an endoscope that observes internal organs such as digestive organs. FIG. 2 is a diagram illustrating a configuration of an examination system and installation of the probe 3. In FIG. 2, a flexible universal cord 14 extending from a side portion of a manipulation unit 13 is connected to a light source device 5 and a signal processing device 6 that processes a subject image captured at a distal end portion 16 of an endoscope 4. The probe 3 is inserted from a probe channel insertion hole 15 in the vicinity of the manipulation unit 13 of an out-of-body portion of the endoscope 4 inserted into the subject. The distal end portion 33 of the probe 3 passes through the inside of an insertion portion 12 and protrudes from an aperture 17 of the distal end portion 16 connected to a probe channel. As a result, the probe 3 is inserted inside the subject, and the optical measurement apparatus 1 starts optical measurement.

Figure 3:
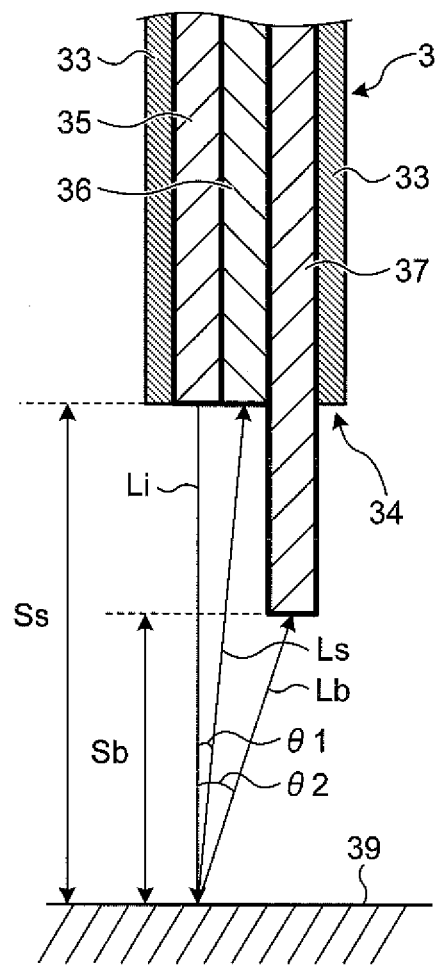
FIG. 3 is a diagram of a distal end portion of the probe illustrated in FIG. 1 cut along a longitudinal direction.
Figure 4:
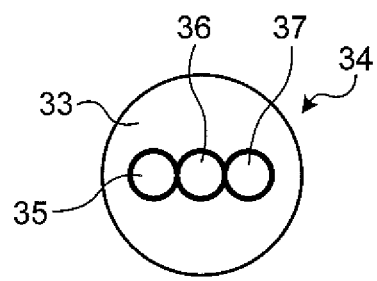
FIG. 4 is a diagram illustrating a distal end surface of the probe illustrated in FIG. 3.

Next, the probe 3 illustrated in FIG. 1 will be described. FIG. 3 is a diagram illustrating the distal end portion 33 of the probe 3 illustrated in FIG. 1. FIG. 3 is a diagram of the distal end portion 33 of the probe 3 illustrated in FIG. 1 cut along a longitudinal direction. FIG. 4 is a diagram illustrating a distal end surface 34 of the probe 3 illustrated in FIG. 3.

As illustrated in FIGS. 3 and 4, the probe 3 includes an illumination fiber 35, a first light detection fiber 36, and a second light detection fiber 37. Each fiber side surface of the illumination fiber 35 and first and second light detection fibers 36 and 37 is covered by a coating layer to shield light and prevent damage.

The illumination fiber 35 propagates the light supplied from the proximal end by the light source unit 22 to the distal end and illuminates light Li from the distal end to an object 39. Each of the first and second light detection fibers 36 and 37 outputs scattered light from the proximal end, which is returned light from the object 39, the returned light entering from the distal end. The detection unit 24 detects the light output from the proximal ends of the first and second light detection fibers 36 and 37.

As illustrated in FIG. 3, the illumination fiber 35 and first and second light detection fibers 36 and 37 are arranged in parallel with one another along a longitudinal direction such that the optical axes thereof are parallel. As illustrated in FIG. 4, the illumination fiber 35 contacts the first light detection fiber 36 at their lateral surfaces, and the second light detection fiber 37 contacts the first light detection fiber 36 at their lateral surfaces. That is, the lateral surface of the illumination fiber 35 contacts one of the first and second light detection fibers 36 and 37, and the lateral surface of the other one of the first and second light detection fibers 36 and 37 contacts the one of the first and second light detection fibers 36 and 37.

Further, positions of distal ends of the first and second light detection fibers 36 and 37 in a longitudinal direction are different from each other. In an example illustrated in FIG. 3, the distal end of the second light detection fiber 37, which is one of the first and second light detection fibers 36 and 37 that is located farther from the illumination fiber 35, is closer to the object 39 in a longitudinal direction than the distal end of the other, which is the first light detection fiber 36. In other words, the positions of the distal ends of the first and second light detection fibers 36 and 37 are set such that a distance Ss between the distal end of the first light detection fiber 36 and the object 39 is greater than a distance Sb between the distal end of the second light detection fiber 37 and the object 39. That is, the distal end of the second light detection fiber 37 protrudes towards the object 39 more than the distal end of the first light detection fiber 36 in a longitudinal direction. In addition, in the example illustrated in FIG. 3, the distal end of the first light detection fiber 36 is set to align with the distal end of the illumination fiber 35.

Figure 5:
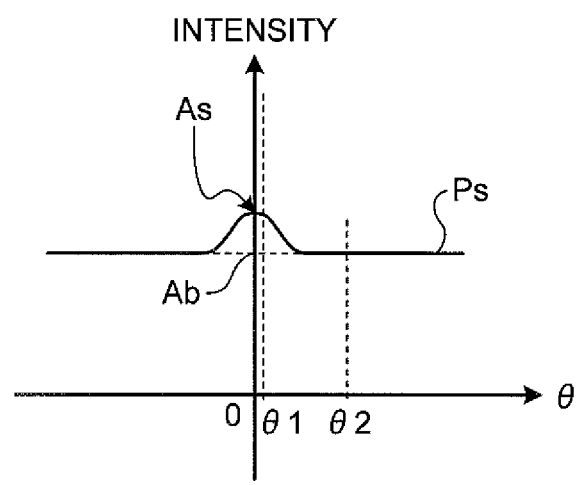
FIG. 5 is a diagram illustrating an angular distribution of scattered light intensity obtained by the optical measurement apparatus according to the first embodiment.

Here, when the LEBS technique is used, as illustrated by a curve Ps indicating scattering angle dependence of scattered light intensity of FIG. 5, analysis is performed by obtaining a peak value As of an interference component of the scattered light and a base value Ab of a baseline not contributing to interference. Thus, in the optical measurement apparatus that measures properties of an subject using the LEBS technique, it is necessary to detect at least two scattered light with different scattering angles $\theta$. For example, in order to obtain a peak value As of an interference component of the scattered light, scattered light having a scattering angle $\theta1$ close to an angle approximately 0° is detected. In addition, in order to obtain a base value Ab of a baseline, scattered light having a scattering angle $\theta2$ greater than at least 1° is detected.

In the first embodiment, the first light detection fiber 36 contacts the illumination fiber 35, and light scattered and reflected at an angle as close to that of the light illuminated from the illumination fiber 35 as possible enters the first light detection fiber 36. Thus, scattered light Ls having a scattering angle $\theta1$ corresponding to the peak value As of the interference component of the scattered light enters the distal end of the first light detection fiber 36.

In addition, since the distal end of the second light detection fiber 37 protrudes towards the object 39 in a longitudinal direction more than the distal end of the first light detection fiber 36, scattered light Lb having a scattering angle $\theta2$ corresponding to a base value Ab, which has a scattering angle greater than the scattering angle $\theta1$, enters the distal end of the second light detection fiber 37. In this manner, the scattering angle $\theta$ of the scattered light entering each light detection fiber is determinable by a distance between the distal end of the light detection fiber and the object 39.

Figure 6:
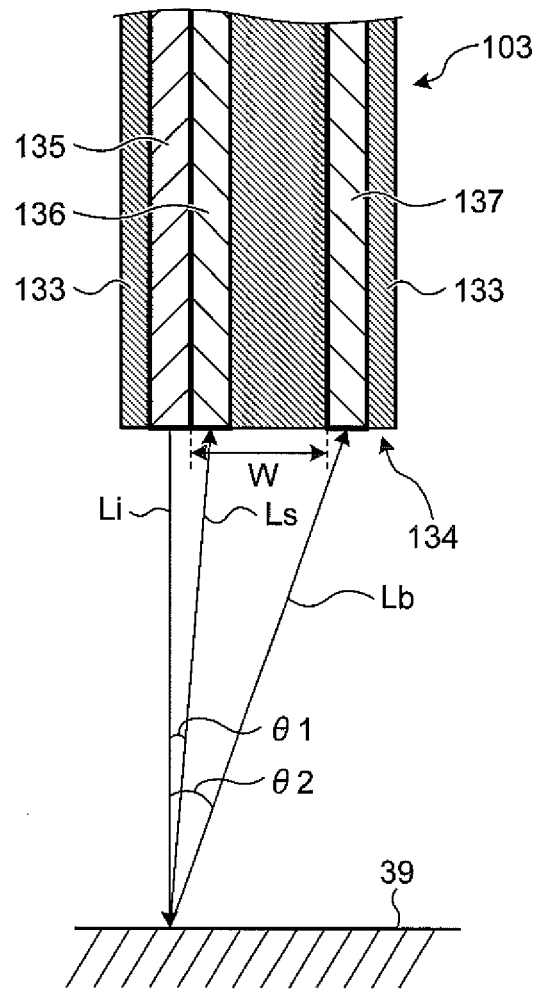
FIG. 6 is a diagram of a distal end portion of a probe of conventional art cut along a longitudinal direction.
Figure 7:
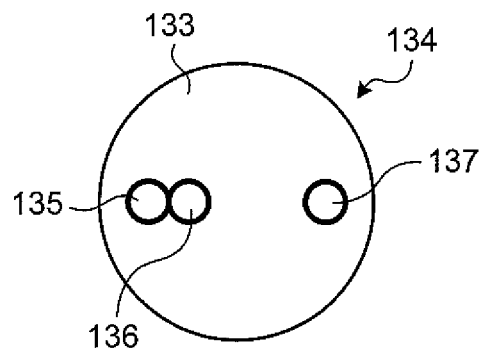
FIG. 7 is a diagram illustrating a distal end surface of the probe illustrated in FIG. 6.

FIG. 6 is a diagram of a distal end portion 133 of a probe 103 of conventional art cut along a longitudinal direction. FIG. 7 is a diagram illustrating a distal end surface 134 of the probe 103 illustrated in FIG. 6. Conventionally, as illustrated by the probe 103 in FIGS. 6 and 7, a first light detection fiber 136 adjacent to a lateral surface of an illumination fiber 135 that emits illumination light Li to an object 39 is provided and scattered light Ls having a scattering angle $\theta1$ is obtained. Further, conventionally, scattered light Lb having a scattering angle $\theta2$ is obtained by providing a second light detection fiber 137 separated from the lateral surface of the illumination fiber 135 by a certain distance W.

Therefore, conventionally, to obtain scattered light having a desired angle, it is necessary to separate the illumination fiber 135 from the second light detection fiber 137 by a certain distance and thus there is a limit to decrease in a diameter of the probe 103.

In contrast, according to the first embodiment, each fiber is arranged such that the distal end of the second light detection fiber 37 protrudes towards the object 39 in a longitudinal direction more than the distal end of the first light detection fiber 36. As a result, it is possible to obtain scattered light Lb having a scattering angle $\theta2$ even if the illumination fiber 35 is adjacent to the second light detection fiber 37. Therefore, according to the first embodiment, since the second light detection fiber 37 that obtains scattered light Lb having a scattering angle $\theta2$ is able to be arranged adjacently to the illumination fiber 35, it is possible to decrease the diameter of the probe 3.

In addition, in the first embodiment, although description has been made for an example in which the position of the distal end of the illumination fiber 35 is aligned with the position of the distal end of the first light detection fiber 36, limitation is not made thereto. Scattered light having a scattering angle even closer to 0° may be obtained by arranging the first light detection fiber 36 such that a position of the distal end of the light detection fiber 36 is located more towards the proximal end of the probe 3 in a longitudinal direction than a position of the distal end of the illumination fiber 35.

First Modification of First Embodiment

Figure 8:
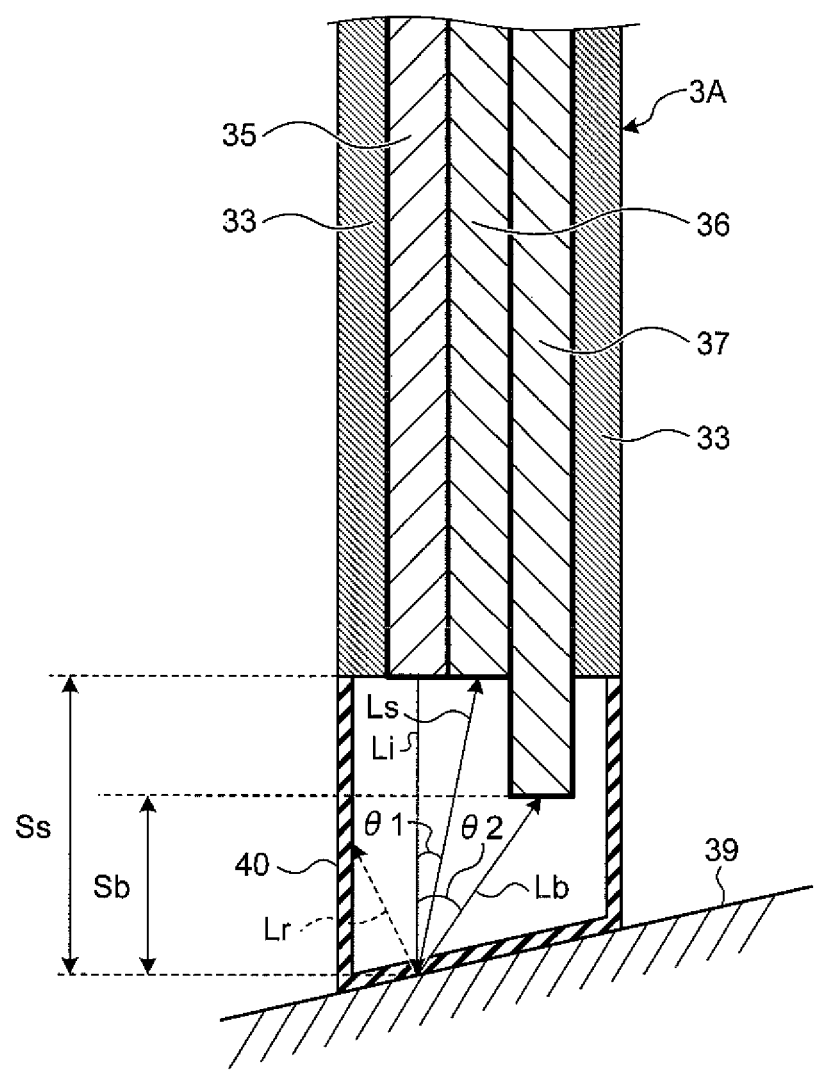
FIG. 8 is a diagram illustrating a distal end portion of a probe according to a first modification of the first embodiment.

Next, a first modification of the first embodiment will be described. FIG. 8 is a diagram illustrating a distal end portion of a probe according to the first modification of the first embodiment. FIG. 8 is a diagram of a distal end portion of the probe cut along a longitudinal direction according to the first modification of the first embodiment.

As illustrated in FIG. 8, a probe 3A according to the first modification of the first embodiment further includes a cap 40 that covers a distal end of an illumination fiber 35, a distal end of a first light detection fiber 36, and a distal end of a second light detection fiber 37.

Here, a spatial coherence length of illumination light is $(\lambda \cdot S)/(\pi \cdot D)$, when $\lambda$ denotes a wavelength of light, S denotes a distance from a light emission surface of an illumination fiber to an object, and D denotes a core diameter of the fiber. The distance between a distal end surface of an illumination fiber 35 and an object 38 is preferably constant in order to perform light illumination with a stable spatial coherence length.

The cap 40 allows light to be illuminated in a state where the distance between the illumination fiber 35 and the object is fixed and the spatial coherence length is infallibly made constant. Further, the cap 40 also allows a distance Ss between the first light detection fiber 36 and an object 39 and a distance Sb between the second light detection fiber 37 and the object 39 to be fixed, and light having a predetermined scattering angle to be stably detected. Furthermore, since the surface of the object 39 is planarized by a bottom surface of the cap 40, measurement is possible without being influenced by concavity and convexity of a surface of the object 39.

In addition, as illustrated in FIG. 8, the bottom surface of the cap 40, which is a contact surface with the object 39, is inclined when viewed from a lateral side of the illumination fiber 35 and the first and second light detection fibers 36 and 37. Due to this inclination of the bottom surface, reflected light at the bottom surface of the cap 40 for the light illuminated from the illumination fiber 35 is reflected, like a path Lr, in a direction different from both a direction towards the distal end of the first light detection fiber 36 and a direction towards the distal end of the second light detection fiber 37. Therefore, it is possible to suppress entrance of reflected light into the first and second light detection fibers 36 and 37, the reflected light being other than the scattered light to be obtained and causing ghost or flare.

Second Modification of First Embodiment

Figure 9:
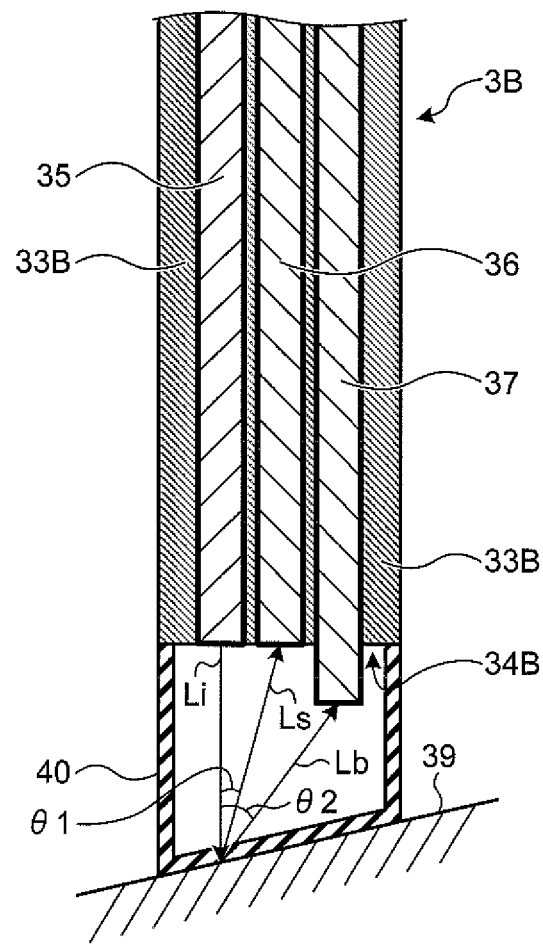
FIG. 9 is a diagram of a distal end portion of a probe cut along a longitudinal direction according to a second modification of the first embodiment.
Figure 10:
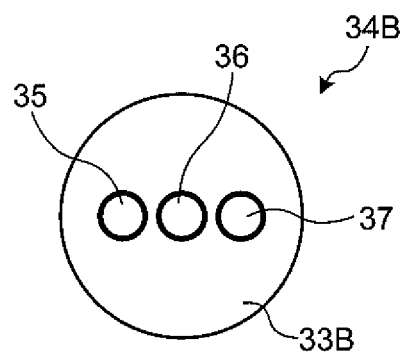
FIG. 10 is a diagram illustrating a distal end surface of the probe illustrated in FIG. 9.

FIG. 9 is a diagram illustrating a distal end of a probe according to a second modification of the first embodiment. FIG. 9 is a diagram of a distal end portion 33B of a probe 3B cut along a longitudinal direction according to the second modification of the first embodiment. FIG. 10 is a diagram illustrating a distal end surface 34B of the probe 3B illustrated in FIG. 9.

Like the probe 3B of FIGS. 9 and 10, an illumination fiber 35 and first and second light detection fibers 36 and 37 are arranged such that their lateral surfaces are each separated from one another. The lateral surfaces of the illumination fiber 35 and the first and second light detection fibers 36 and 37 are not necessarily in contact with any thereof, and arrangement of the illumination fiber 35 and the first and second light detection fibers 36 and 37 may be adjusted such that scattered light Ls having a scattering angle θ1 is incident on the distal end of the first light detection fiber 36, and scattered light Lb having a scattering angle θ2 is incident on the distal end of the second light detection fiber 37.

Third Modification of First Embodiment

Figure 11:
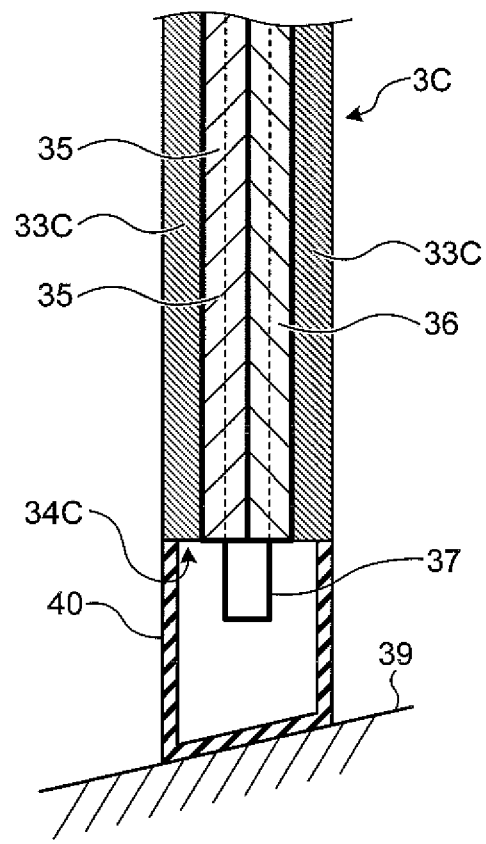
FIG. 11 is a diagram of a distal end portion of a probe cut along a longitudinal direction according to a third modification of the first embodiment.
Figure 12:
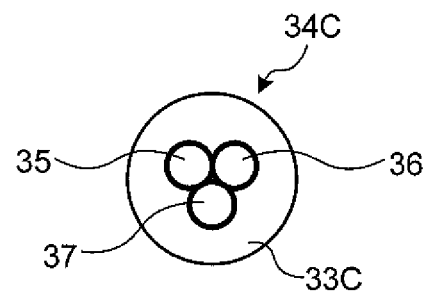
FIG. 12 is a diagram illustrating a distal end surface of the probe illustrated in FIG. 11.

FIG. 11 is a diagram illustrating a distal end portion of a probe according to a third modification of the first embodiment. FIG. 11 is a diagram of a distal end portion 33C of a probe 3C cut along a longitudinal direction according to the third modification of the first embodiment. FIG. 12 is a diagram illustrating a distal end surface 34C of the probe 3C illustrated in FIG. 11.

As illustrated in FIGS. 11 and 12, an illumination fiber 35 and first and second light detection fibers 36 and 37 contact one another at their lateral surfaces. That is, optical axes of these fibers may not be coplanar.

When the illumination fiber 35 and the first and second light detection fibers 36 and 37 are arranged like this, it is possible to further decrease a diameter of the probe 3C.

Fourth Modification of First Embodiment

Figure 13:
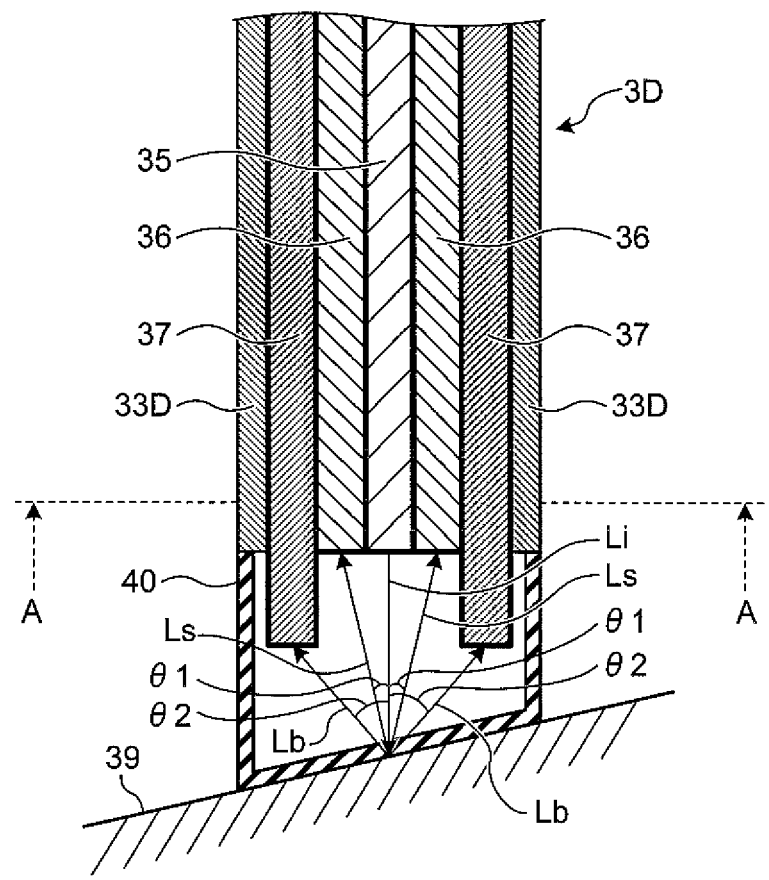
FIG. 13 is a diagram of a distal end portion of a probe cut along a longitudinal direction according to a fourth modification of the first embodiment.
Figure 14:
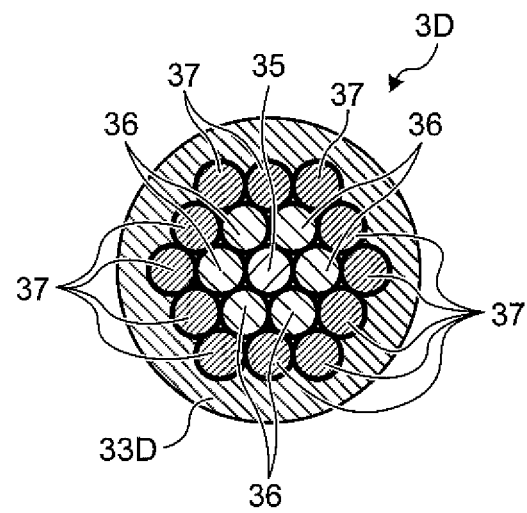
FIG. 14 is a diagram illustrating a cross section of the probe illustrated in FIG. 13 cut along line A-A.

FIG. 13 is a diagram illustrating a distal end portion of a probe according to a fourth modification of the first embodiment. FIG. 13 is a diagram of a distal end portion 33D of a probe 3D cut along a longitudinal direction according to the fourth modification of the first embodiment. FIG. 14 is a diagram illustrating a cross section of the probe 3D cut along line A-A illustrated in FIG. 13.

As illustrated in FIGS. 13 and 14, in the probe 3D according to the fourth modification of the first embodiment, a multiple number of first light detection fibers 36 are arranged such that their distal ends are located at positions in which scattered light Ls having a scattering angle θ1 enters. Further, in the probe 3D, a multiple number of second light detection fibers 37 are arranged such that their distal ends are located at positions in which scattered light Lb having a scattering angle θ2 enters.

As described, by using a group of fibers including a multiple number of fibers, it is possible to obtain more scattered light of the same angle.

Second Embodiment

Figure 15:
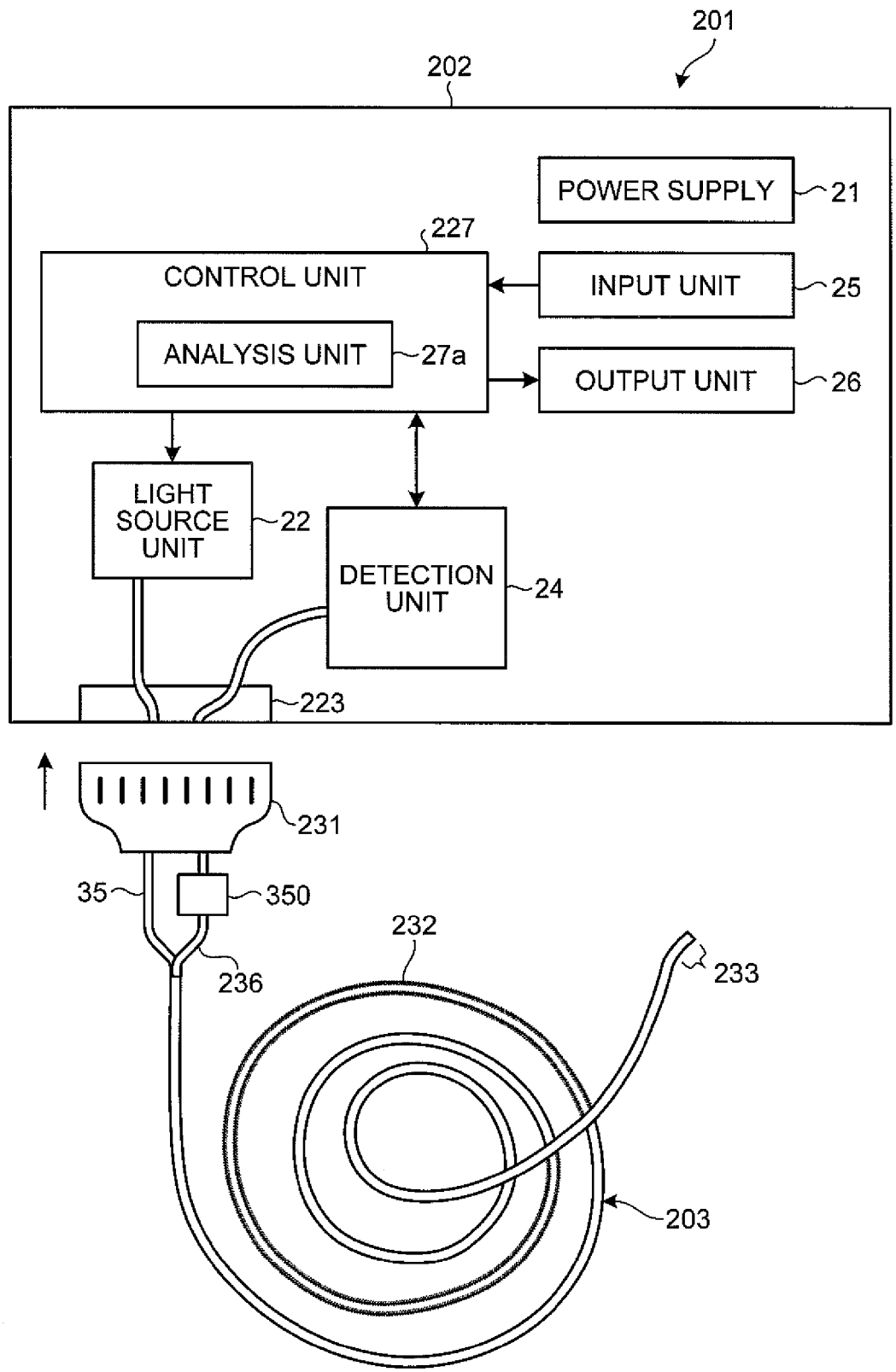
FIG. 15 is a schematic diagram illustrating a schematic configuration of an optical measurement apparatus according to a second embodiment.

Next, a second embodiment will be described. Scattered light having different scattering angles are obtained by moving a position of a distal end of a light detection fiber. FIG. 15 is a schematic diagram illustrating a schematic configuration of an optical measurement apparatus according to the second embodiment.

As illustrated in FIG. 15, an optical measurement apparatus 201 according to the second embodiment has a main unit 202 instead of the main unit 2 illustrated in FIG. 1 and a probe 203 instead of the probe 3 illustrated in FIG. 1.

The main unit 202 includes a connector 223 that outputs scattered light output from a probe 203 to a detection unit 24 and a control unit 227 having a function similar to that of the control unit 27. Similarly to the probe 3, the probe 203 includes a proximal end portion 231 detachably connected to the connector 223 of the main unit 202, a flexible portion 232 having flexibility, and a distal end portion 233 from which light supplied from a light source unit 22 is emitted and into which scattered light from an object to be measured enters. The probe 203 is movable in a longitudinal direction with the illumination fiber 35 and has a light detection fiber 236 (see FIG. 16) that outputs, from a proximal end thereof, the scattered light from the object, the scattered light entering from a distal end thereof. Further, the probe 203 has a mover 350 that relatively moves the light detection fiber 236 with respect to the illumination fiber 35 in a longitudinal direction.

Figure 16:
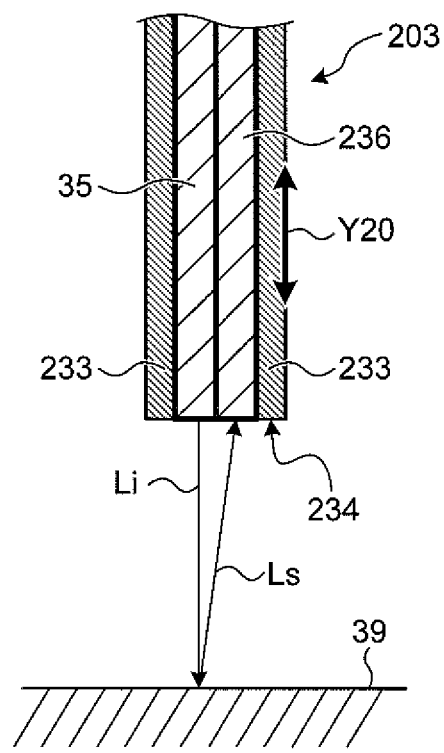
FIG. 16 is a diagram of a distal end portion of a probe illustrated in FIG. 15 cut along a longitudinal direction.
Figure 17:
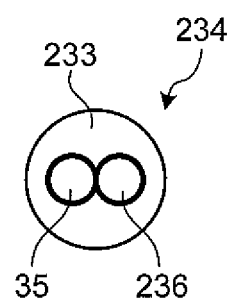
FIG. 17 is a diagram illustrating a distal end surface of the probe illustrated in FIG. 16.

FIG. 16 is a diagram illustrating the distal end portion 233 of the probe 203 illustrated in FIG. 15. FIG. 16 is a diagram of the distal end portion 233 of the probe 203 illustrated in FIG. 15 cut along a longitudinal direction. FIG. 17 is a diagram illustrating a distal end surface 234 of the probe 203 illustrated in FIG. 16.

As illustrated in FIGS. 16 and 17, the illumination fiber 35 and the light detection fiber 236 are arranged in parallel with each other along a longitudinal direction such that their optical axes are parallel with each other. As illustrated in FIG. 17, the illumination fiber 35 contacts the light detection fiber 236 at their lateral surfaces.

Figure 18:
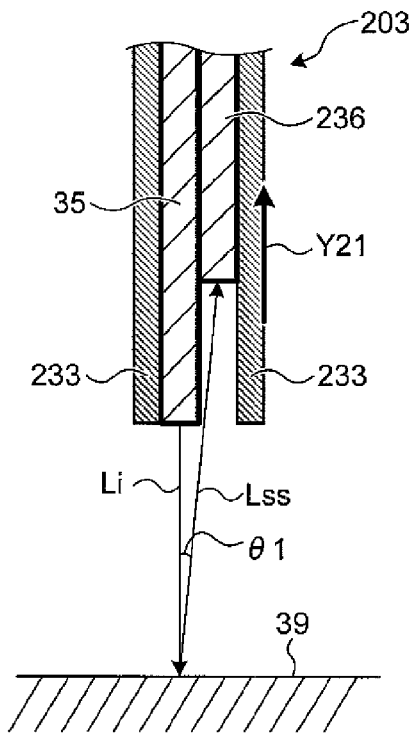
FIG. 18 is a diagram illustrating movement of a light detection fiber illustrated in FIG. 16.

As indicated by an arrow Y20 of FIG. 16, the light detection fiber 236 is movable in both a forward direction and a backward direction along a longitudinal direction corresponding to an optical axis direction within the probe 203 by a moving process of the mover 350. As indicated by an arrow Y21 of FIG. 18, the light detection fiber 236 moves, by the movement process of the mover 350, the light detection fiber such that the distal end of the light detection fiber 236 is located closer to the proximal end of the illumination fiber 35 than the distal end of the illumination fiber 35. In this case, scattered light Lss having a scattering angle $\theta 1$ close to approximately 0° is incident on the distal end of the light detection fiber 236. The detection unit 24 detects scattered light Lss having a scattering angle $\theta 1$ output from the proximal end of the light detection fiber 236, and an analysis unit 27a obtains a peak value As of an interference component of the scattered light. The mover 350 may move the light detection fiber 236 such that the distal end of the light detection fiber 236 is located at the same position as that of the distal end of the illumination fiber in a longitudinal direction as long as the scattered light Lss having the scattering angle $\theta 1$ enters therein.

Figure 19:
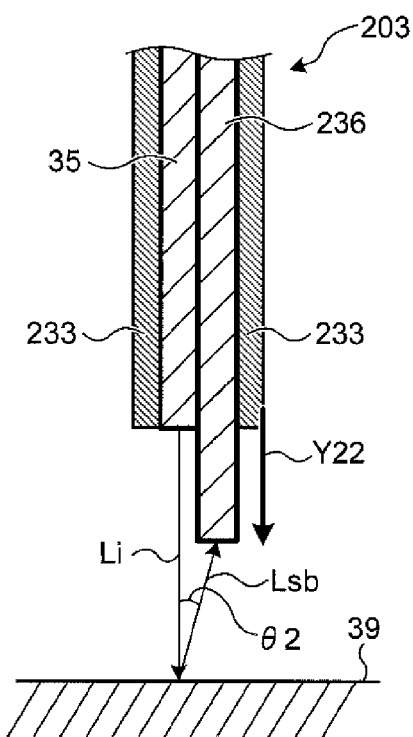
FIG. 19 is a diagram illustrating movement of the light detection fiber illustrated in FIG. 16.

Next, as indicated by an arrow Y22 of FIG. 19, the light detection fiber 236 is moved by the movement process of the mover 350 such that the distal end of the light detection fiber 236 in an optical axis direction protrudes from the distal end of the illumination fiber 35 in a longitudinal direction. In this case, scattered light Lsb having a scattering angle $\theta 2$ greater than approximately 1° is incident on the distal end of the light detection fiber 236. The detection unit 24 detects the scattered light Lsb having the scattering angle $\theta 2$ output from the proximal end of the light detection fiber 236, and the analysis unit 27a obtains a base value Ab of a baseline not contributing to interference. The analysis unit 27a analyzes characteristics of an object 39 based on the base value Ab of the baseline not contributing to interference and the peak value As of the interference component of the scattered light Lsb, which are obtained as described.

In this manner, according to the second embodiment, the mover 350 is able to move the light detection fiber 236 such that the distal end of the light detection fiber 236 is located at a first position and a second position different from the first position in a longitudinal direction of the light detection fiber 236. The detection unit 24 detects each of returned light entering from the distal end of the light detection fiber 236 at the first position and returned light entering from the distal end of the light detection fiber 236 at the second position. The analysis unit 27a measures properties of the object based on a result of the detection by the detection unit 24 corresponding to the first and second positions.

Therefore, according to the second embodiment, since scattered light of a plurality of angles are obtainable with one light detection fiber 236 and one optical detector by moving the light detection fiber 236 along the longitudinal direction, it is possible to reduce the number of light detection fibers than in the first embodiment. Therefore, according to the second embodiment, it is possible to further decrease a diameter of the probe 203.

Figure 20:
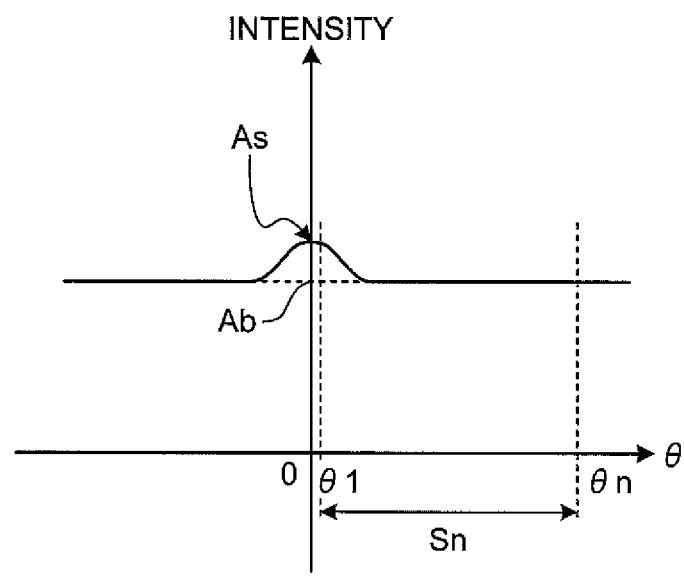
FIG. 20 is a diagram illustrating an angular distribution of scattered light intensity obtained by the optical measurement apparatus according to the embodiment.

In addition, according to the second embodiment, it is possible to obtain scattered light of any scattering angle within an angle range Sn from a scattering angle $\theta 1$ to a scattering angle $\theta n$ that corresponds to a position adjacent to the object 39 as illustrated in FIG. 20 by adjusting a movement position of the distal end of the light detection fiber 236 along the longitudinal direction. Therefore, according to the second embodiment, it is possible to obtain a plurality of scattered light intensity profiles.

Figure 21:
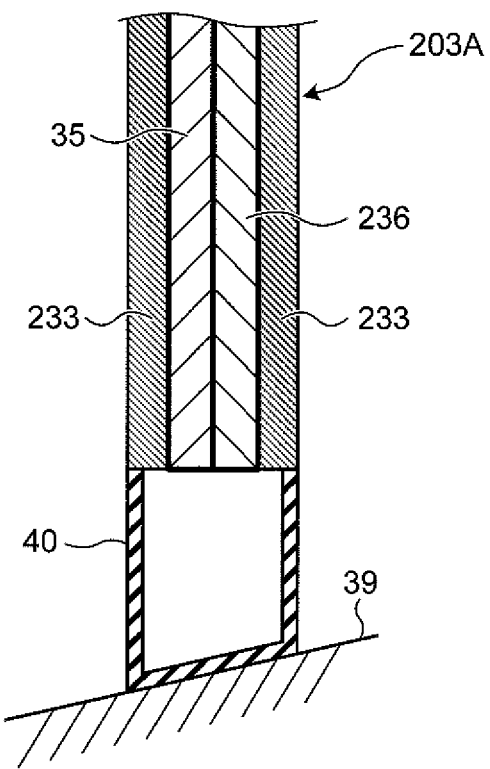
FIG. 21 is a diagram illustrating another example of the distal end portion of the probe illustrated in FIG. 15 cut along a longitudinal direction.
Figure 22:
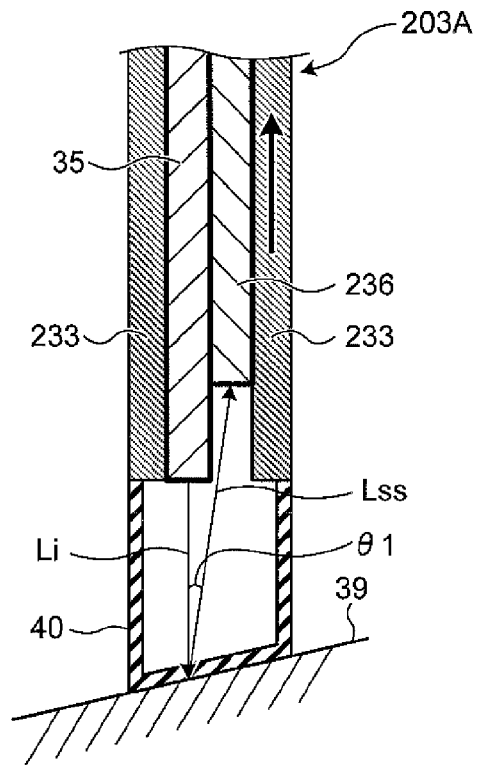
FIG. 22 is a diagram illustrating movement of a light detection fiber illustrated in FIG. 21.
Figure 23:
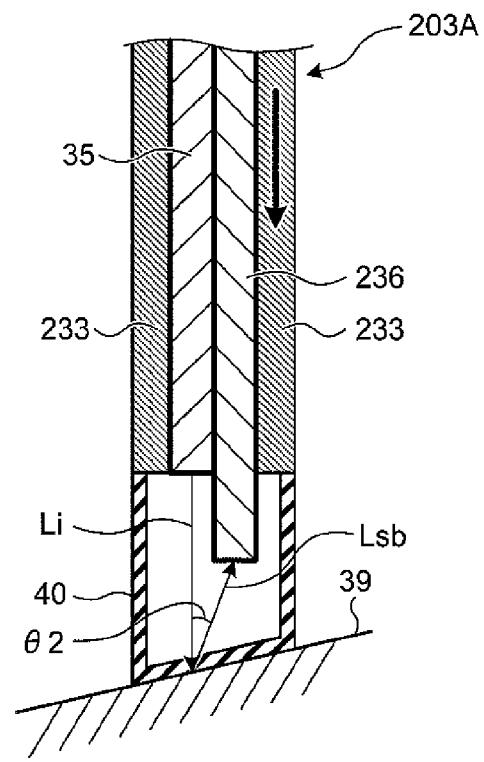
FIG. 23 is a diagram illustrating movement of the light detection fiber illustrated in FIG. 21.

In addition, according to the second embodiment, like a probe 203A illustrated in FIG. 21, a cap 40 that covers a distal end of an illumination fiber 35 and a distal end of a light detection fiber 236 may be further provided. It is possible to remove influence of concavity and convexity on a surface of an object 39 by the cap 40 and stabilize a distance between the distal end of the light detection fiber 236 and the object 39, when the light detection fiber 236 is moved to a proximal end side as indicated by an arrow of FIG. 22. Therefore, it is possible to stably detect scattered light Lss having a scattering angle $\theta 1$. Similarly, when the light detection fiber 236 is moved to protrude more than the distal end of the illumination fiber 35 as indicated by an arrow of FIG. 23, it is possible to remove influence of a surface shape of the object 39 by the cap 40 and stabilize a distance between the distal end of the light detection fiber 236 and the object 39. In this case also, it is possible to stably detect scattered light Lsb having a scattering angle $\theta 2$.

Figure 24:
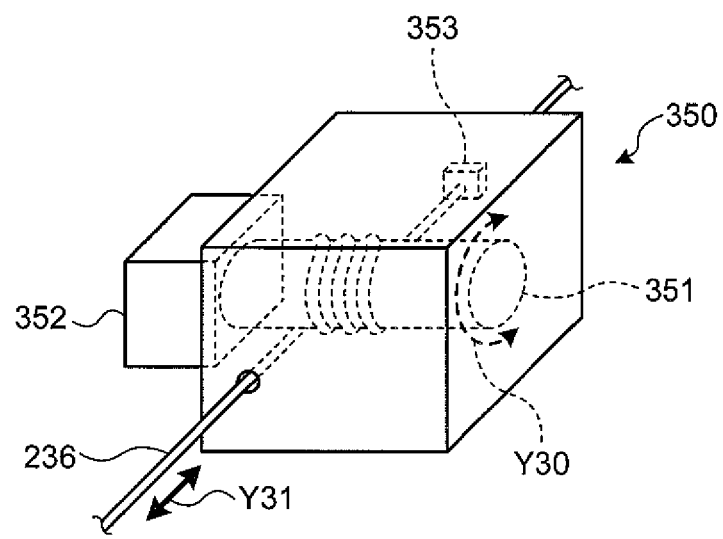
FIG. 24 is a perspective view illustrating a mover illustrated in FIG. 15.
Figure 25:
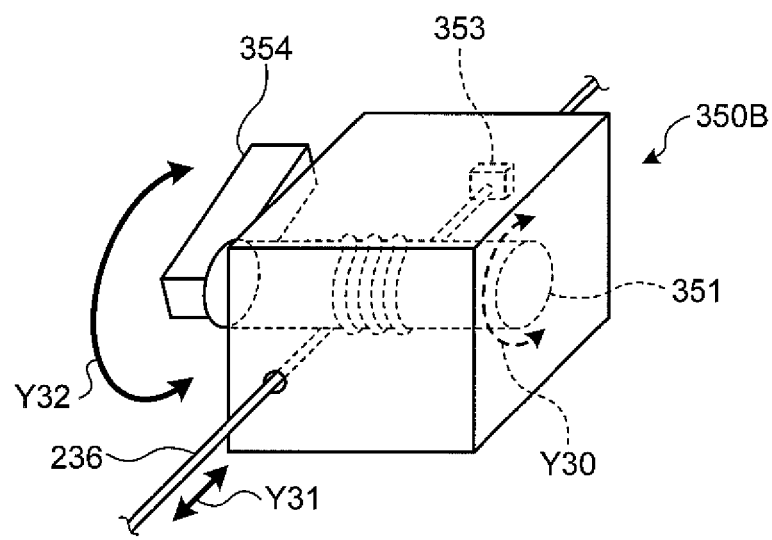
FIG. 25 is a perspective view illustrating another example of the mover illustrated in FIG. 15.

Next, the mover 350 will be described. FIG. 24 is a perspective view illustrating the mover 350 illustrated in FIG. 15. As illustrated in FIG. 24, the mover 350 has, inside thereof, a configuration in which the light detection fiber 236 is wound around a rotational shaft 351, with a part being a fixed end of the light detection fiber 236, the part at a proximal end side of the light detection fiber 236, the part fixedly connected by a fixed member 353, and with the distal end of the light detection fiber 236 being a free end. The rotational shaft 351 rotates as indicated by an arrow Y30 by drive of a rotational driving unit 352 including a motor or the like. The rotational driving unit 352 includes, for example, an input switch not illustrated and rotates the rotational shaft 351, by manipulation of the input switch, in a direction in which the light detection fiber 236 is wounded, or rotates the rotational shaft 351 in a direction in which the light detection fiber 236 is unwound. A case in which at the distal end of the probe 203, a position of the distal end of the illumination fiber 35 and a position of the distal end of the light detection fiber 236 are aligned together will be described as a reference. The light detection fiber 236 is moved therefrom in a longitudinal direction as indicated by an arrow Y31 by winding or unwinding the light detection fiber 236 by rotation of the rotational shaft 351. Like a mover 3502 of FIG. 25, the rotational shaft 351 may be configured to rotate in synchronization with rotation of a handle 354 as indicated by an arrow Y32. Driving of the rotational driving unit 352 is configured to be controlled by the control unit 27 such that driving to a position at which scattered light of a desired angle is receivable is performed based on an instruction from the manipulation unit 13 or the input unit 25.

Figure 26:
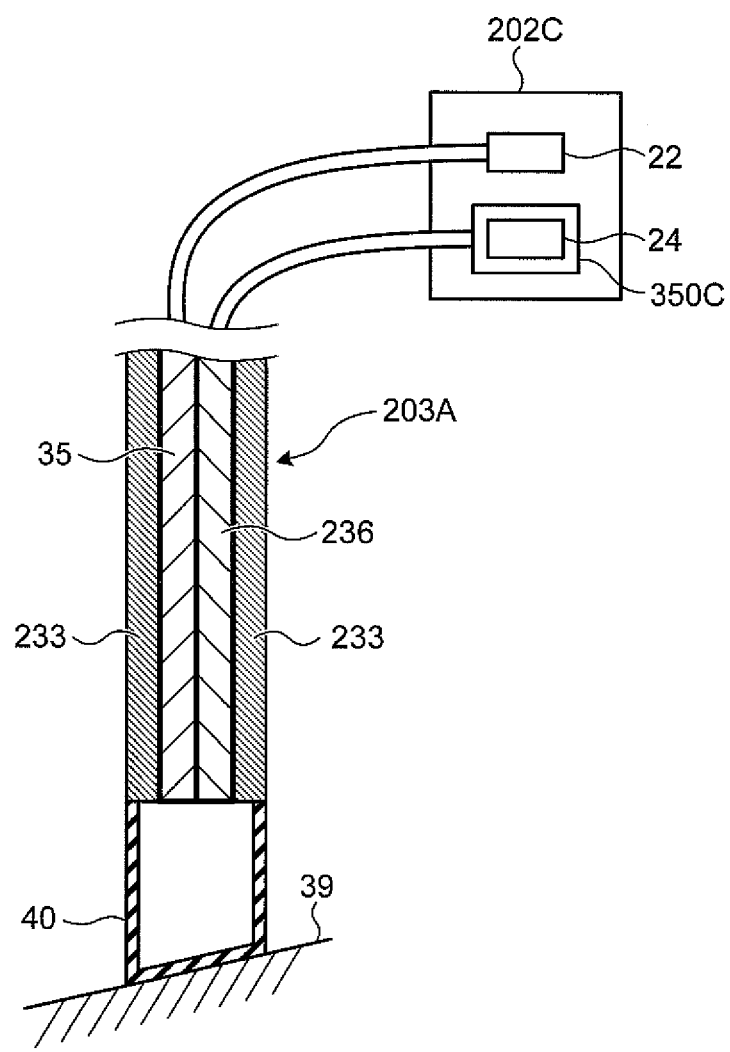
FIG. 26 is a perspective view illustrating another example of the mover illustrated in FIG. 15.
Figure 27:
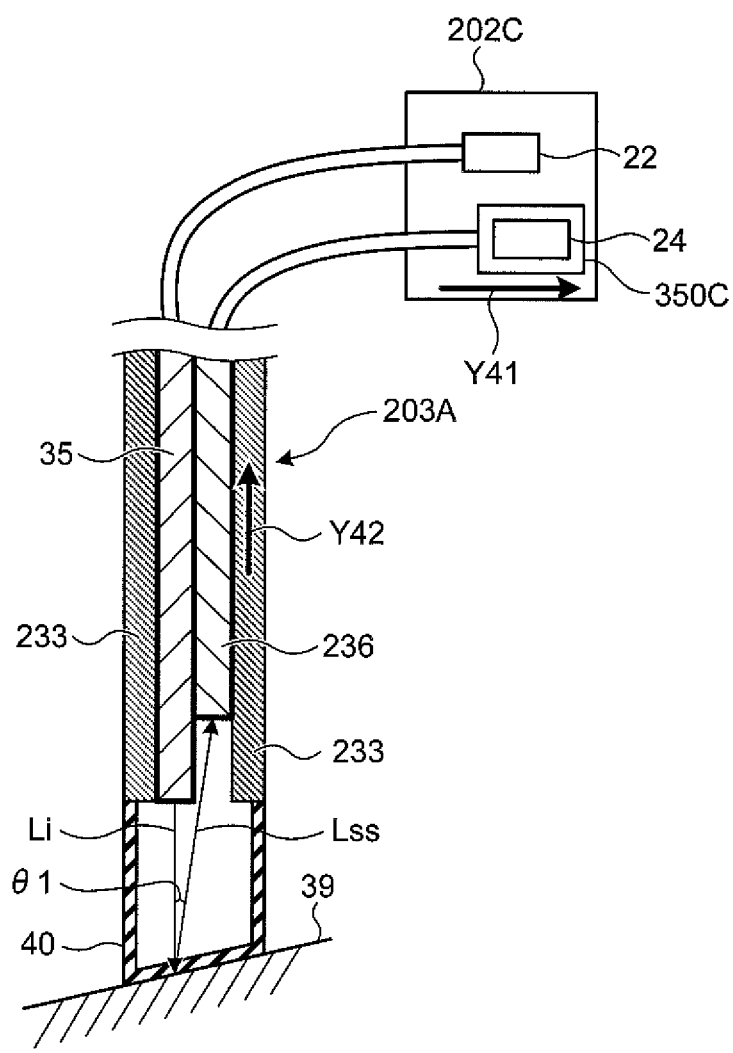
FIG. 27 is a diagram illustrating movement of a light detection fiber illustrated in FIG. 26.
Figure 28:
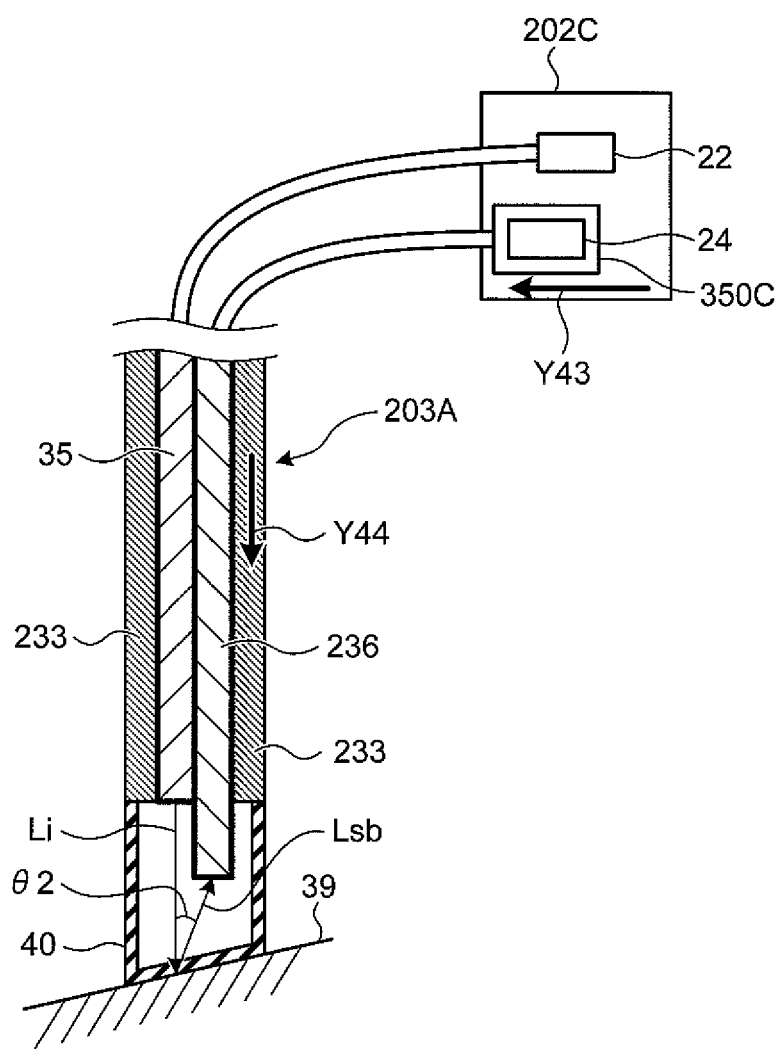
FIG. 28 is a diagram illustrating movement of the light detection fiber illustrated in FIG. 26.

The whole detection unit 24 to which the light detection fiber 236 is connected may be moved in order to move the light detection fiber 236. As illustrated in FIG. 26, in a main unit 202C, a movement mechanism 350C having an actuator and the like that move a detection unit 24 is provided. Driving of this movement mechanism 350C is configured to be controlled by a control unit 27 such that driving to a position at which scattered light having a desired angle is receivable is performed based on an instruction from a manipulation unit 13 or an input unit 25. When the detection unit 24 is moved away from a connector of a main unit 2020 by the movement process of the movement mechanism 350C as indicated by an arrow Y41 of FIG. 27, a distal end of a light detection fiber 236 is also moved to a proximal end side in synchronization with this movement as indicated by an arrow Y42. As a result, the light detection fiber 236 is able to detect scattered light Lss having a scattering angle θ1 at the distal end. In addition, when the detection unit 24 is brought close to a connector side of the main unit 202C by the movement process of the movement mechanism 350C as indicated by an arrow Y43 of FIG. 28, the distal end of the light detection fiber 236 protrudes towards the object 39 more than the distal end of the illumination fiber 35 in synchronization with this movement as indicated by an arrow Y44. As a result, the light detection fiber 236 is able to detect scattered light Lsb having a scattering angle θ2 at the distal end. In this case also, a cap 40 may be provided on the distal end of the probe 203A to remove influence of concavity and convexity of a surface of an object 39 and stabilize a distance between the distal end of the light detection fiber 236 and the object 39.

According to an embodiment of the present invention, because the positions, in the longitudinal direction, of the distal ends of the first and second light detection fibers differ from each other, even if the illumination fiber is adjacent to the first and second light detection fibers, it is possible to obtain scattered light having a desired scattering angle and to decrease the diameter of the probe.

According to another embodiment of the present invention, because the light detection fiber is movable in a longitudinal direction, by moving in the longitudinal direction with respect to the illumination fiber, even if the illumination fiber is adjacent to the light detection fiber, it is possible to obtain scattered light having a desired scattering angle and to decrease the diameter of the probe.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical measurement apparatus that measures a property of a scatterer by using a low-coherence enhanced backscattering technique, the optical measurement apparatus comprising:
a light source configured to supply, as illumination light, incoherent light having a short spatial coherence length and at least one spectral component;
an illumination fiber configured to propagate, to a distal end of the illumination fiber, light supplied from a proximal end of the illumination fiber by the light source and illuminates light onto the scatterer from the distal end;
a first light detection fiber configured to output, from a proximal end of the first light detection fiber, a first returned light from the scatterer at a first scattering angle that is substantially the same as an angle of the light illuminated from the illumination fiber;
a second detection fiber having a distal end configured to protrude towards the scatterer in a longitudinal direction more than the distal end of the first light detection fiber, the second detection fiber being configured to output, from a proximal end of the second detection fiber, a second returned light from the scatterer at a second scattering angle greater than the first scattering angle;
a detection unit configured to detect: (1) the first returned light that is output from the proximal end of the first light detection fiber to obtain a peak value of an interference component of the illumination light, and (2) the second returned light output from the proximal end of the second light detection fiber to obtain a base value of a baseline; and
a measurement unit configured to measure a property of the scatterer based on the peak value and the base value obtained by the detection unit.

2. The optical measurement apparatus according to claim 1, further comprising a cap that covers the distal end of the illumination fiber, the distal end of the first light detection fiber, and the distal end of the second light detection fiber.

3. The optical measurement apparatus according to claim 2, wherein a contact surface between the cap and the scatterer is inclined when viewed from a lateral side of the illumination fiber and the first and second light detection fibers.

4. The optical measurement apparatus according to claim 1, wherein the illumination fiber and the first and second light detection fibers are arranged such that their optical axes are in parallel with one another.

5. The optical measurement apparatus according to claim 1, wherein the distal end of one of the first and second light detection fibers that is located farther from the illumination fiber is closer to the scatterer in a longitudinal direction than the distal end of the other one of the first and second light detection fibers.

6. The optical measurement apparatus according to claim 1, wherein a lateral surface of the illumination fiber contacts one of the first and second light detection fibers, and a lateral surface of the other one of the first and second light detection fibers contacts the one of the first and second light detection fibers.

7. The optical measurement apparatus according to claim 1, wherein lateral surfaces of the illumination fiber and the first and second light detection fibers contact one another.

8. The optical measurement apparatus according to claim 1, wherein each of the first and second light detection fibers includes a multiple number of fibers.

9. The optical measurement apparatus according to claim 1, wherein the light source is an incoherent light source.

10. The optical measurement apparatus according to claim 1, further comprising a probe for measurement, the probe being detachably connected, wherein the probe includes the illumination fiber and the first and second light detection fibers.

11. A probe for measurement detachably connected to an optical measurement apparatus that measures a property of a scatterer by using a low-coherence enhanced backscattering technique, the probe comprising:
an illumination fiber configured to propagate, to a distal end of the illumination fiber, illumination light supplied from a proximal end of the illumination fiber by a light source and illuminates light onto the scatterer from the distal end;
a first light detection fiber configured to output, from a proximal end of the first light detection fiber, a first returned light from the scatterer at a first scattering angle that is substantially the same as an angle of the light illuminated from the illumination fiber; and a second detection fiber having a distal end configured to protrude towards the scatterer in a longitudinal direction more than the distal end of the first light detection fiber, the second detection fiber being configured to output, from a proximal end of the second detection fiber, a second returned light from the scatterer at a second scattering angle greater than the first scattering angle, wherein the optical measurement apparatus includes:
- a detection unit configured to detect: (1) the first returned light that is output from the proximal end of the first light detection fiber to obtain a peak value of an interference component of the illumination light, and (2) the second returned light output from the proximal end of the second light detection fiber to obtain a base value of a baseline, and
- a measurement unit configured to measure a property of the scatterer based on the peak value and the base value obtained by the detection unit.

12. The probe according to claim 11, further comprising a cap that covers the distal end of the illumination fiber, the distal end of the first light detection fiber, and the distal end of the second light detection fiber.

13. The probe according to claim 12, wherein a contact surface between the cap and the scatterer is inclined when viewed from a lateral side of the illumination fiber and the first and second light detection fibers.

14. The probe according to claim 11, wherein the illumination fiber and the first and second light detection fibers are arranged such that their optical axes are in parallel with one another.

15. The probe according to claim 11, wherein the distal end of one of the first and second light detection fibers that is located farther from the illumination fiber is closer to the scatterer in a longitudinal direction than the distal end of the other one of the first and second light detection fibers.

16. The probe according to claim 11, wherein a lateral surface of the illumination fiber contacts one of the first and second light detection fibers, and a lateral surface of the other one of the first and second light detection fibers contacts the one of the first and second light detection fibers.

17. The probe according to claim 11, wherein lateral surfaces of the illumination fiber and the first and second light detection fibers contact one another.

18. The probe according to claim 11, wherein each of the first and second light detection fibers includes a multiple number of fibers.

* * * * *